United States Patent
Koshizuka et al.

[11] Patent Number: 5,534,999
[45] Date of Patent: Jul. 9, 1996

[54] MONITORING SUB-MICRON PARTICLES

[75] Inventors: Hiroshi Koshizuka, Shiga-ken; Takashi Kanatake, Saitama-ken, both of Japan

[73] Assignee: Shinmikuni Kikai Ltd., Osaka, Japan

[21] Appl. No.: 383,683

[22] Filed: Feb. 1, 1995

Related U.S. Application Data

[63] Continuation of Ser. No. 26,970, Mar. 5, 1993, abandoned.

[51] Int. Cl.$^6$ .......................... G01N 21/00; G01N 15/02
[52] U.S. Cl. .......................... 356/338; 356/336; 356/343
[58] Field of Search .................... 356/336, 338, 356/343

[56] References Cited

U.S. PATENT DOCUMENTS

| | | | |
|---|---|---|---|
| 4,178,103 | 12/1979 | Wallace | 356/338 |
| 4,408,880 | 10/1983 | Tsuji et al. | 356/338 |
| 4,522,494 | 6/1985 | Bonner | 356/338 |
| 4,577,964 | 3/1986 | Hansen, Jr. | 356/338 |
| 4,842,406 | 6/1989 | Von Bargen | 356/338 |
| 4,850,707 | 7/1989 | Bowen et al. | 356/338 |
| 4,917,496 | 4/1990 | Sommer | 356/338 |
| 5,037,202 | 8/1991 | Batchelder et al. | 356/338 |
| 5,085,500 | 2/1992 | Blesener | 356/338 |
| 5,125,737 | 6/1992 | Rodriguez et al. | 356/338 |
| 5,142,140 | 8/1992 | Yamazaki et al. | 356/338 |

FOREIGN PATENT DOCUMENTS

| | | |
|---|---|---|
| 62-803 | 1/1987 | Japan. |
| 63-19535 | 1/1988 | Japan. |
| 4-9635 | 2/1992 | Japan. |

*Primary Examiner*—Rolf Hille
*Assistant Examiner*—David Ostrowski
*Attorney, Agent, or Firm*—Kerkam, Stowell, Kondracki & Clarke; William L. Feeney

[57] ABSTRACT

Sub-micron particles in fluid such as ultrapure water are detected or monitored by a simple apparatus in which a light beam from a coherent light source (1) is converged (2) in such a manner that the light beam is focussed in a stream (3) of particle-containing fluid, the light passed through the stream and diffracted by the particles is received by a photo-detector (4) which is positioned at an opposite side of the coherent light source with respect to the stream and substantially on an optical axis of the light beam, so that the number of particles in the stream is counted from electrical signals emitted by the photo-detector.

16 Claims, 5 Drawing Sheets

MONITORING SUB-MICRON PARTICLES

This is a continuation of application Ser. No. 08/026,970, filed Mar. 5, 1993, now abandoned.

BACKGROUND OF THE INVENTION

1. Field of the Invention

The present invention relates to a method and apparatus for monitoring or detecting sub-micron particles on a novel principle which is completely different from the conventional techniques.

The method according to the present invention is advantageously applicable to monitor and control impurity particles in fluids such as pure water and ultrapure water used in electronics industries, biotechnology, medical and pharmaceutical application and foods industries. The present method can be used to evaluate the performance of separation membranes and filtration systems.

2. Related Arts

The conventional methods for monitoring or detecting particles in fluid are classified into following four categories:

(1) Shadow system in which decrement of light intensity caused by travelling particles in fluid passing across an optical axis of parallel ray.

(2) Microscope system in which fine particles in fluid are caught by a membrane filter or the like and are observed or counted by a electron scanning microscope.

(3) Light scattering system in which fluid is irradiated with an intensive light such as a laser beam and the resulting scattered light is collected by a lens so that the focused light is detected by an photo-multiplier (4) Imaging system in which a fluid is irradiated with a light and the resulting contrast of light is detected by a photo-diode alley and an image of particles in the fluid is formed by a computer.

New techniques such as ultrasonic scattering technique are also proposed.

In the case of the shadow system (1), however, detection of fine particles is limited to the particle size of about 1 μm and hence this detection system can not be used for sub-micron particles. In the microscope system (2), more than half day is required to obtain the result.

The light scattering system (3) is the main current of development in particle counters or detectors and now ultra-fine particles having the particle size of less than 0.07 μm can be detected by using a light source having shorter wave length such as argon laser. In fact, Japanese patent laid-open No. 4-39,635 discloses a technique to determine the precise number of fine contaminant particles each having the particle size of lower than 0.07 μm contained in ultrapure water. This patent proposes to use two detectors each receive the scattered light so that a particle counter produces a signal when two detectors detect the scattered light simultaneously. This system, however, requires a high-power laser as well as very sensitive photo-multiplier, resulting in a large costly system. Still more, in this system, precise alignment between an axis of fluid stream containing particles to be detected and an optical axis is required in order to assure the reliability of measurement. Japanese patent laid-open No. 62-803 discloses an automated apparatus which facilitates this alignment.

Japanese patent laid-open No. 63-19535 discloses a variation of the imaging system (4). In this patent, a laser beam impinges vertically to a flow of sample liquid and the diffracted and scattered light is passed through a Fourier-transformation optical system or a lens to produce a Fraunhofer diffraction image which is treated in order to evaluate fine particles in the liquid. In this patent, a diameter of a laser beam is enlarged to obtain a parallel ray which is directed to the sample liquid. This system requires a complicated computer system.

Therefore, an object of the present invention is to provide a method which permits to detect fine particles of sub-micron as contaminant in fluid, in particular, pure water or ultrapure water by a simple and very economical apparatus.

SUMMARY OF THE INVENTION

The present invention provides a method for detecting sub-micron particles in fluid comprising converging a light beam from a coherent light source so that the resulting focussed light passes through a stream of fluid containing particles therein in such a manner that a focus of the focussed light is located in the stream of fluid, receiving a light passed through the stream of fluid and diffracted by the particles by a photodetector which is positioned at an opposite side of the coherent light source with respect to the stream and on an optical axis of the light beam to produce electrical signals, and counting numbers of particles in the stream by treating the electrical signals.

The present invention provides also an apparatus for detecting sub-micron particles in fluid comprising a coherent light source, an optical system for converging a light beam emitted out of the coherent light source to produce a converged light, a cell through which a stream of fluid containing particles flows and being located in the neighborhood of a focus of the converged light beam, a photo-detector which is positioned at an opposite side of the coherent light source with respect to the stream and on an optical axis of the light beam to produce electrical signals, and an electric circuit for counting numbers of particles in the stream by treating the electrical signals.

The coherent light source is preferably a laser diode and the photodetector comprises preferably at least one photo-diode, more preferably a photo-diode alley arranged perpendicularly to the direction of the stream and also perpendicularly to the optical axis. The optical system can be a lens. Preferably, the electric circuit includes differential amplifiers for multiplying signals from elements in the photo-detector alley. The cell can be a part of a transparent tube through which a stream of fluid containing particles flows.

The present invention is based on such surprising and unexpected finding that the existence of sub-micron particles in a liquid stream can be detected or monitored by utilizing diffraction phenomenon of a transmitted light, which is observed when a converged coherence light is focussed on the liquid stream. In fact, it is not known to use the transmitted light of a converged light directly for detecting fine particles. In the conventional detection technique, dispersed particles are irradiated with an illumination parallel ray so that the resulting transmitted light image is Fourier-transformed as is described in the Japanese patent laid-open No. 63-19,535.

The detection principle of the method according to the present invention is different from those of known methods but the theory why the particles in fluid is detected precisely by the method according to the present invention can not be explained completely at this stage. Following is one of probable explanations.

Now, we will refer to attached drawings.

Figure 2:
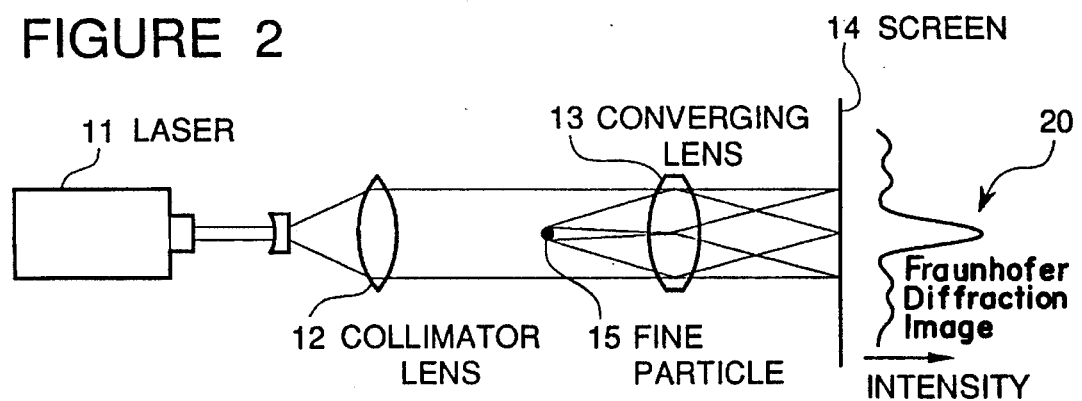
FIG. 2 is an illustration for explaining a conventional technique.

At first, the conventional detection method is explained with referring to FIG. 2 in which a fine particle (15) is irradiated with a parallel ray produced by a laser (11) and collimator lens (12) and the resulting diffracted light is converged by a lens (13). In this case, so-called Fraunhofer diffraction image (20) shown at the right side of FIG. 2 is observed. Fraunhofer diffraction is a well-known physical phenomenon which is used in particle counters. A general term of "diffraction" is used to define "all phenomena that can't be explained by the linearity of light" and can be described by Fresnel-Huygens' principle. However, according to this principle, the case when the radius of a particle becomes lower than a wave length of light used can't be explained by the Fraunhofer diffraction phenomenon but is described as scattering phenomenon of light. In fact, if the radius of a particle becomes smaller than a wave length of light used, the diffraction can't occur any more in a parallel ray because each particle functions like a point source and scatters light In much detailed scientific theory, the diffraction phenomenon is explained as a kind of scattering phenomenon and can be described by the Mie scattering theory which is derived strictly from the Maxwell's electro-magnetic equation. Since the Mie scattering theory is complicated and is difficult to be handled, an approximated equation is generally made in the relation between the radius "r" of a particle and the wave length "$\lambda$" of light used (Rayleigh scattering for "r<$\lambda$", Mie scattering for the case when "r is nearly equal to $\lambda$", Fraunhofer scattering for "r>$\lambda$").

According to the conventional Fraunhofer diffraction theory of a parallel ray, the divergent angle $\Delta\theta$ of diffraction caused by an obstruction or fine particle is represented by an equation of $\Delta\theta=1.22\ \lambda/D$, in which "D" is a diameter of the particle (D=2r). The divergent angle $\Delta\theta$ of diffraction increases with decrement of the diameter of the particle and becomes to 90° when D is equal to 0.78 $\lambda$. Usually, this value of the divergent angle $\Delta\theta$ is the detection limit, so that the detectable minimum particle size is 0.52 µm at a wave length $\lambda=0.67$ µm. In fact, a diffraction image of a particle whose particle size is lower than a wave length used is not easily obtainable in experiments.

The present inventors found surprisingly such a fact that, when a particle is placed in the neighborhood of a focus of a converged beam focussed by a lens, the diffraction angle becomes so small so that such finer particles becomes detectable, even if their particle sizes are smaller than the wave length used. On this finding, the present inventors completed the present invention which provides a novel method which permits to detect sub-micron particles. The most important advantage of the method according to the present invention in industry reside in that sub-micron particles can be detected at high sensitivity and with high precision by a simple combination of a cheap laser (light source) and a cheap photo-diode (pickup).

In the method according to the present invention, the diffracted image can be obtained for a particle whose particle size is smaller than 0.1 µm which is not observable in known techniques. Of course, particles having the particle size of bigger than 0.1 µm also can be detectable with high sensitivity by the method according to the present invention.

DESCRIPTION OF THE PREFERRED EMBODIMENT

Now, the present invention will be described with referring to drawings but the present invention should not be limited to an embodiment shown in the drawings.

Figure 1:
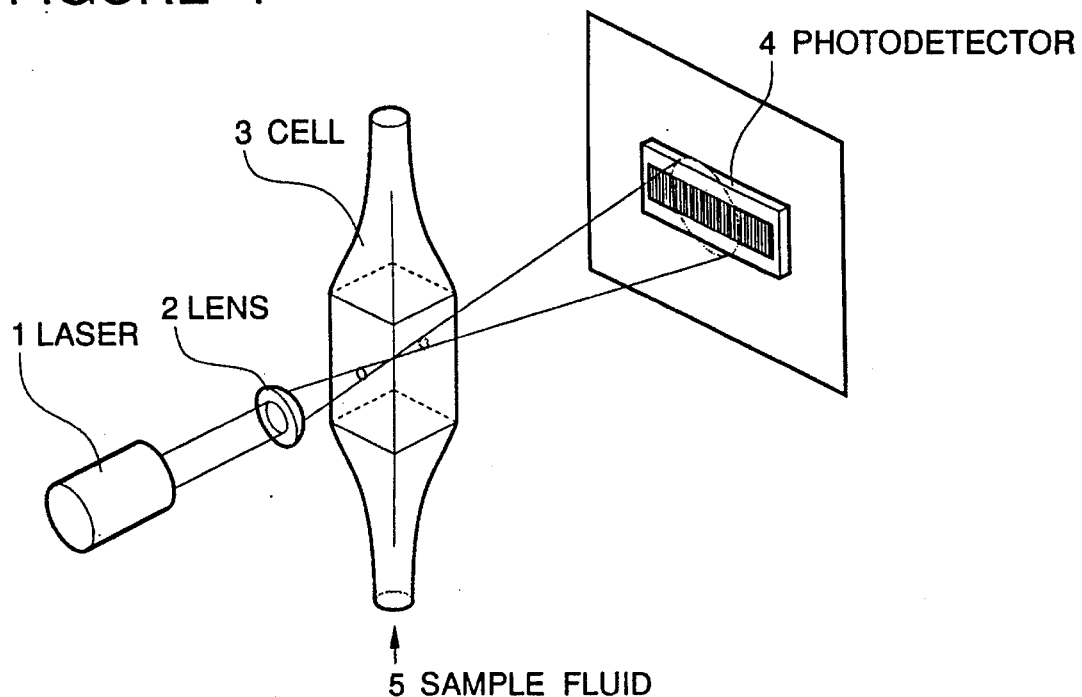
FIG. 1 is a perspective view illustrating the principle of the detection method according to the present invention.

An apparatus for monitoring or detecting fine particles shown in FIG. 1 illustrating principle of the detection method according to the present invention comprises a laser (1) as a coherent light source, an optical system, preferably a lens (2) for converging a light beam emitted out of the coherent light source to produce a converged light, a cell (3) through which a stream (5) of fluid containing particles flows, which is located in the neighborhood of a focus of the converged light beam, a photo-detector (4) which is positioned at an opposite side of the coherent light source (1) with respect to the stream and substantially on an optical axis of the light beam such as a photo-diode or a photo-diode alley, and an electric circuit (not shown) for converting the resulting light intensity signals or a diffraction image detected by the photo-detector (4) to electrical signals from which numbers of particles in the stream is counted. All elements used in the present invention are available on market and are very cheap.

Figure 3:
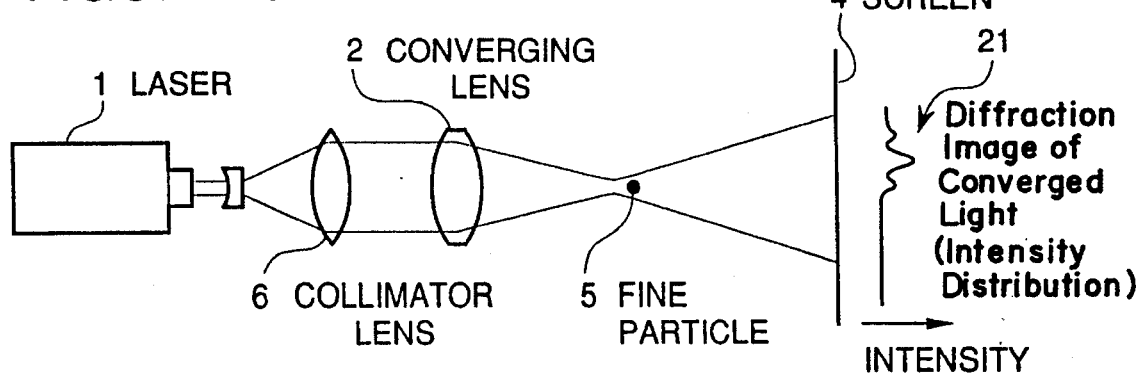
FIG. 3 is an illustration similar to FIG. 2 but is for explaining the detection method according to the present invention.

The coherent light source may consist of a laser (1) and a collimator lens system (6) (FIG. 3). The laser (1) can be any laser but is preferably a laser diode or semiconductor laser of small power. In other words, a cheap laser diode can be used advantageously in the method according to the present invention. Sensitivity increases with decrement of the wave length of laser oscillation. Inventors confirmed that the detection principle of the present invention can be applicable for a laser diode whose power is smaller than 1 mW, for example 0.2 mW.

The focal distance of the optical system or lens (2) for converging a light beam is determined in function of the particle size to be detected. For example, a lens having the focal distance f=10 mm may be used to detecting a fine particle whose particle size is 0.2 µm.

The cell (3) must be transparent at least on light-receiving face and light exiting face but can have a very simple structure because no consideration is required to stray light. In other words, the light from the converging lens 2 may go directly to the cell 3, meaning that no light shields or lenses are disposed therebetween. The cell (3) has not necessarily a rectangular section shown in FIG. 1 but can have any section. The cell (3) can be a separate piece from a tube for a stream of fluid containing particles but, according to another advantage of the present invention, is preferably a part of a transparent tube through which the stream of fluid containing particles flows. Thus, the portion of the fluid stream on which the laser is focused is either larger in cross sectional area than the tube (as shown) or the same diameter or cross sectional area as the tube leading to the cell. The focus is located in a focus portion of the stream of fluid which has a cross sectional area at least as great as a maximum cross sectional area in portions of the stream of fluid upstream and downstream relative to the focus portion. The transparent tube can be made of fluoro resin in order to resist chemicals.

In practice, a suitable adjusting mechanism is preferably used for positioning the optical system (2) so that the focused beam is focuses in the neighborhood of the center of the cell (3).

Not so high sensitivity is required in the photo-detector (4) if the photo-detector (4) can detect the diffraction image hidden in the transmitted light. In this sense, photo-diode can be used. The photo-detector (4) can comprise a single photo-diode but preferably constitutes of a photo-diode alley. The photo-diode alley is preferably arranged perpendicularly to the direction of the stream and also perpendicularly to the optical axis. As shown in FIG. 1, the light goes directly from the fluid stream to the photodetector 4, meaning that there are no lenses therebetween.

The diffraction image or the distribution of intensity of a converged light observed in the photo-detector (4) used in the apparatus according to the present invention is illustrated at the right side of FIG. 3.

In practice, signals from elements in the photo-detector alley are multiplied in differential amplifiers to improve the SN ratio of the photo-detector (4) in such a manner that an electric signal of zero is produced when the elements in the photo-detector alley are irradiated uniformly or no particle passes through the cell (3), while suitable electric signal which represents characteristics (number, size etc) of the particles is produced when any change in intensity caused by the diffraction image of a converged light is appeared in the elements in the photo-detector alley.

Figure 4:
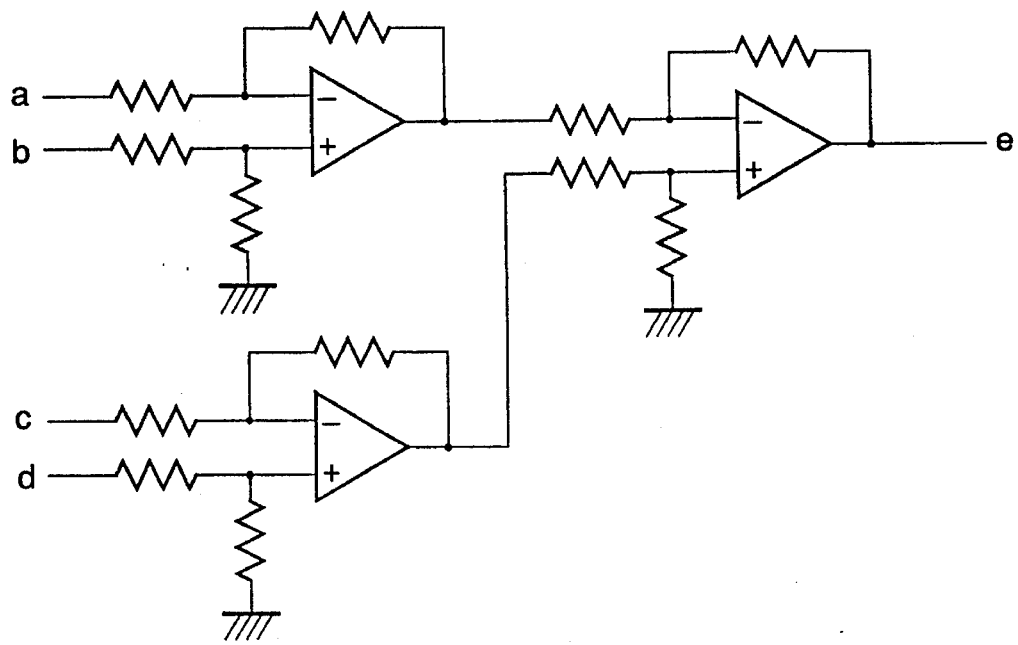
FIG. 4 is an example of a differential amplifier used in an apparatus according to the present invention.

FIG. 4 illustrates an example of differential amplifiers for a photo-detector alley consisting of four photo-diode elements. The values of resistances in the differential amplifiers of FIG. 4 are adjusted in such a manner that zero output signal (e) is produced when identical output signals are produced at the output (a to d) of all photo-diode elements or the all photo-diode elements are irradiated with a light of identical intensity. Therefore, the output signal (e) of the differential amplifiers of FIG. 4 changes when any change in intensity is appeared in the output signal, for example (a) of the photo-diode elements.

In the embodiments shown in FIG. 1 and FIG. 3, all elements of a laser (1), a lens (2), a cell (3) and a photo-diodes (4) are arranged on a straight line but they can be arranged on non-linear line by using suitable mirror(s) in known manner so as to reduce the total size or length of the apparatus.

Now, Examples of the monitoring/detection method according to the present invention will be shown in Examples.

EXAMPLE 1

Fine particles were detected by using the principle shown in FIG. 1 under following conditions and procedure:

| Experiment conditions | |
| --- | --- |
| Laser: | Semiconductor laser (wave length = 670 nm, power = 0.5 mW) |
| Focal distance of a converging lens: | 10 mm |
| Liquid tested: | ultrapure water |
| Flow rate of the liquid: | 100 mm/sec |
| Diameter of fine particles added: | 0.208 µm |
| Photo-detector: | photo-diode alley (32 elements) |
| Differential amplifiers: | FIG. 4 |

Experiment procedure

Figure 5:
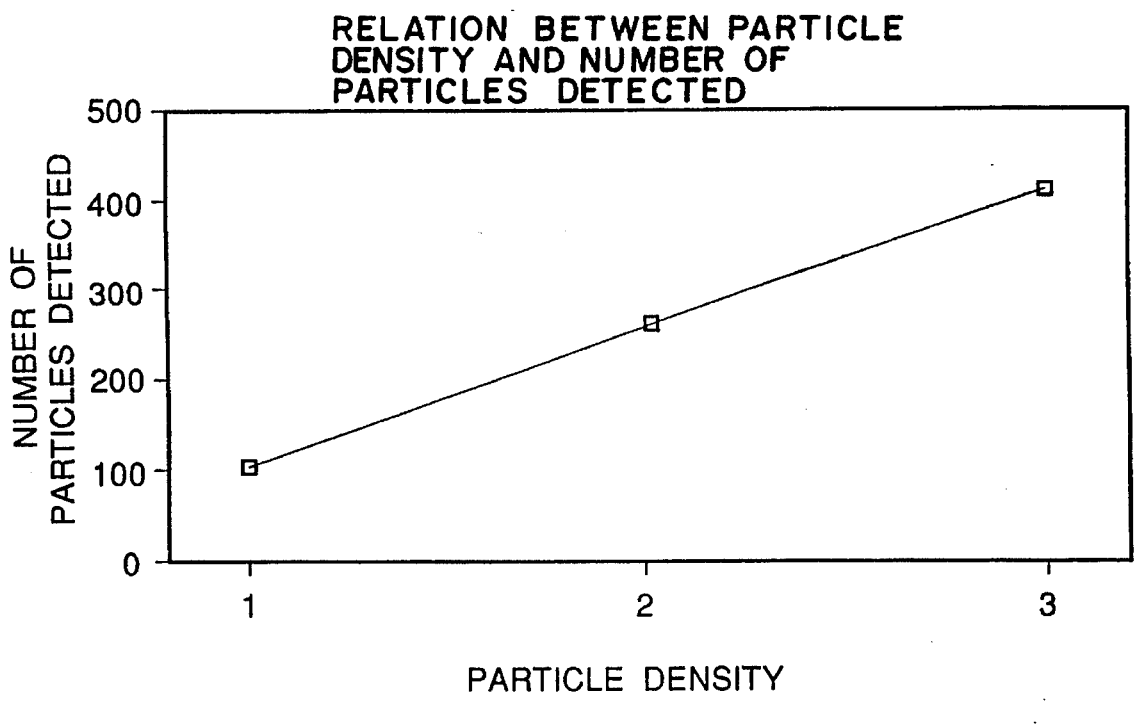
FIG. 5 and FIG. 6 are graphs each showing a relation between the particle density in fluid and the number of particles detected in Example 1 and 2.

Three liquid samples having different particle concentrations (dilution of 1 to 3 times) were prepared and flows at a rate of 120 ml/min through the apparatus illustrated in FIG. 1. The resulting change in the number of particles detected is shown in FIG. 5.

This Example reveals such a fact that the method according to the present invention is applicable to detect a particle having the particle size of 0.208 µm.

EXAMPLE 2

Example 1 was repeated but the particle size of particles introduced in ultrapure water was changed to 0.1 µm.

Figure 6:
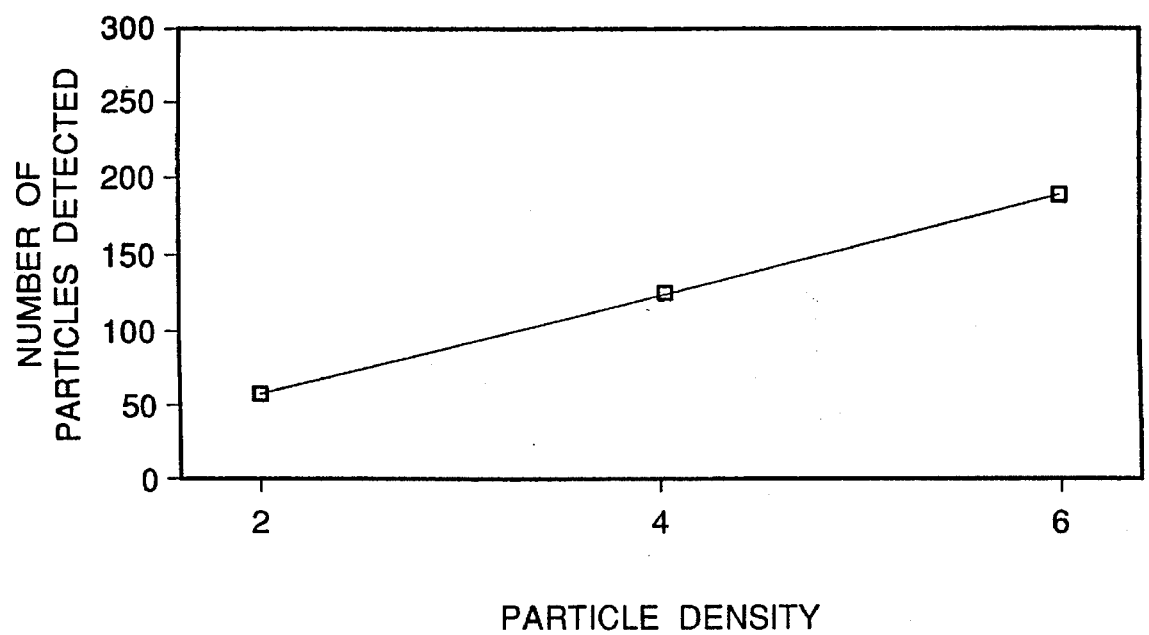

The resulting change in the number of particles detected is shown in FIG. 6. This Example reveals that the method according to the present invention is applicable to a system for detecting particles having the particle size of 0.1 µm.

EXAMPLE 3

The method according to the present invention was applied to ultrapure water produced in an actual industrial water purification unit.

Figure 7:
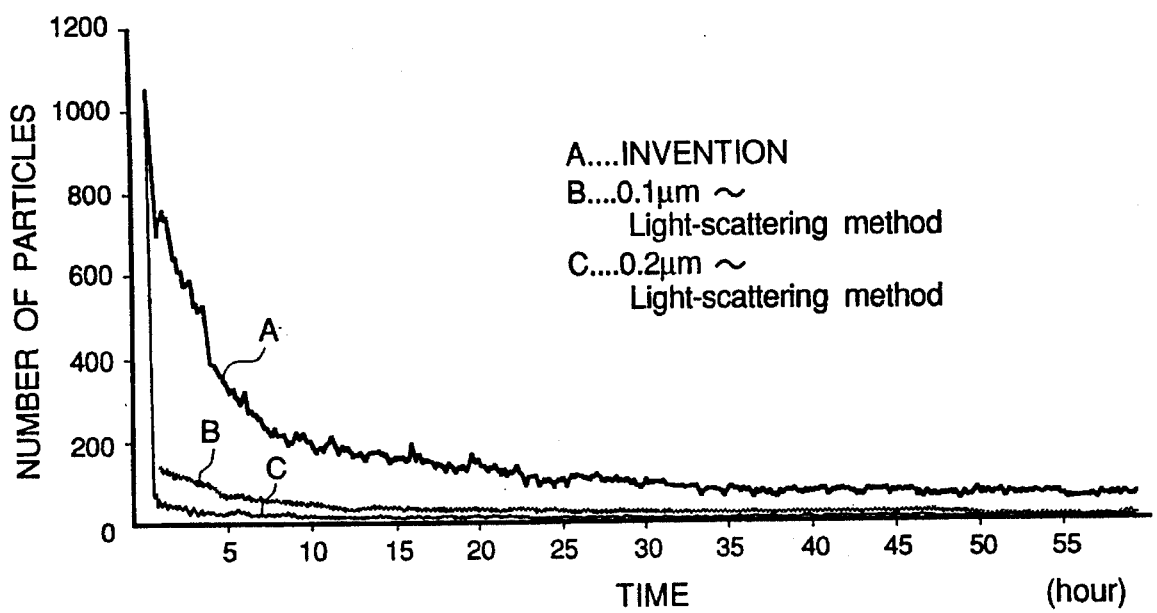
FIG. 7 and FIG. 8 are graphs each showing a relation between the number of particles detected in ultrapure water after an ultrapurification unit starts at different contamination levels
Figure 8:
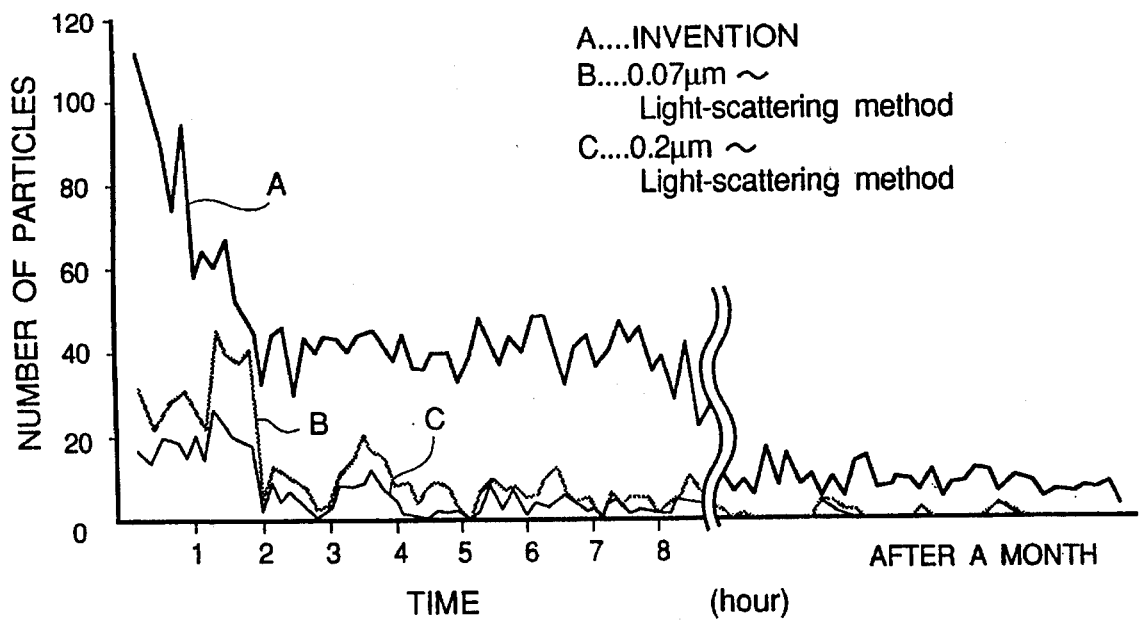

A curve "A" in FIG. 7 shows a relation between the number of particles detected (arbitrary unit) by the method according to the present invention and time duration after the purification unit starts.

For comparison, the same liquid sample was tested in two detectors of known scattering method. Two curves "B" and "C" in FIG. 7 show the results obtained by the known scattering systems in which makers of the detectors indicate that particles above 0.1 µm and 0.2 µm are detectable respectively.

EXAMPLE 4

Example 3 was repeated for another ultrapure water which is much purified than Example 3.

The results of Example 3 and 4 reveal such a fact that much numbers of particles are detectable in the method according to the present invention comparing to the conventional scattering method.

From FIG. 5 to 8, it is apparent that the number of particles detected by the method according to the present invention is substantially in proportion to the number of particles actually present in liquid or to the number of particles detected by the conventional scattering method. Therefore, the method according to the present invention can be used as a particle counter by using a suitable calibration curve.

EXAMPLE 5

The method according to the present invention was applied to ultrapure water left in ambient atmosphere. Namely, the purity of ultrapure water was examined daily for four days. The results are shown in FIG. 9.

Figure 9:
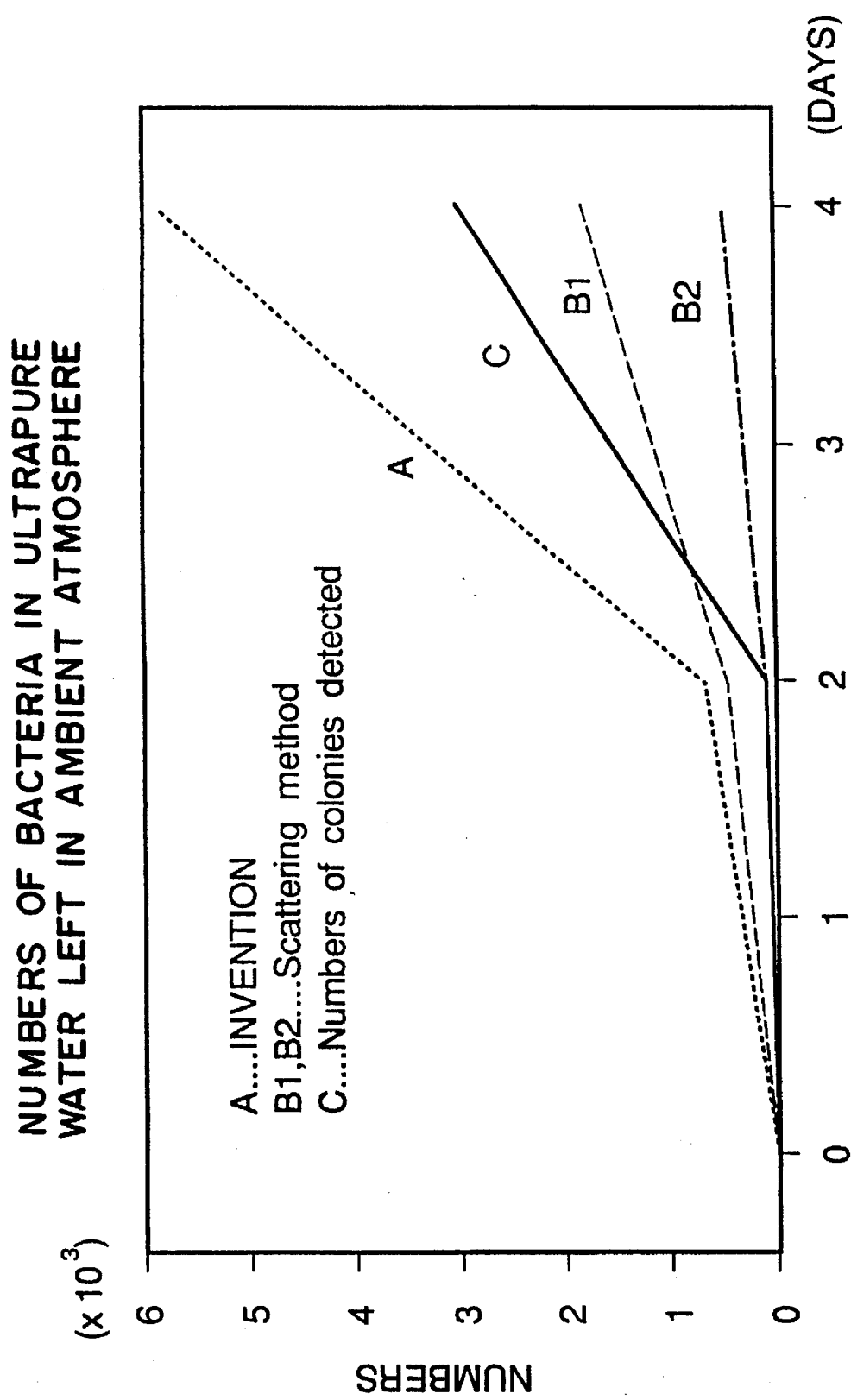
FIG. 9 shows graphs of development in contamination with bacteria in ultrapure water left in ambient for four days.

In FIG. 9, a curve "C" show a relation between time duration (days) and the number of colonies determined by a known culture technique in which ultrapure water samples were cultured on medium.

Three curves of "A" and "B1, B2" are overlapped with the curve "C" in FIG. 9. The result of the method according to the present invention is shown by the curve "A", while curves of "B1, B2" correspond to the conventional scattering method.

FIG. 9 reveals such a fact that the result obtained by the method according to the present invention has a stronger resemblance to the actual value than the conventional scattering method. This means that the method according to the present invention is suitable in medial uses or pharmaceutical uses.

What is claimed is:

1. A method for measuring sub-micron particles in a fluid comprising converging a light beam from a coherent light source (1) so that the resulting focussed light passes through a stream (3) of fluid containing particles therein in such a manner that a focus of the focussed light is located in said stream (3) of fluid, receiving a light passed through said stream (3) and diffracted by said particles by means of a photo-detector (4) which is positioned at an opposite side of said coherent light source (1) with respect to said stream (3) and substantially on an optical axis of said light beam to produce electrical signals, and treating said electrical signals from said photo-detector (4) to count a number of particles in said stream by using a predetermined calibration curve; and wherein said focus is located in a focus portion of said stream of fluid which has a cross sectional area at least as great as a maximum cross sectional area in portions of said stream of fluid upstream and downstream relative to said focus portion.

2. The method set forth in claim 1 wherein said coherent light source is a laser diode.

3. The method set forth in claim 1 wherein said photo-detector comprises a photo-diode alley.

4. The method set forth in claim 3 wherein said fluid is pure water or ultrapure water.

5. The method set forth in claim 1 wherein said fluid is pure water or ultrapure water.

6. The method of claim 1 wherein the light goes directly from the stream of fluid to the photodetector.

7. The method of claim 6 wherein the focused light goes directly from a focusing lens to the stream of fluid.

8. The method of claim 1 wherein the focused light goes directly from a focusing lens to the stream of fluid.

9. An apparatus for measuring sub-micron particles in a fluid comprising a coherent light source (1), an optical system (2) for converging a light beam emitted out of said coherent light source to produce a converged light, a cell (3) through which a stream of fluid containing particles is flows and being located in the neighborhood of a focus of said converged light beam, a photo-detector (4) which is positioned at opposite side of said coherent light source (1) with respect to said stream and substantially on an optical axis of said light beam to produce electrical signals, and an electric circuit for treating said electrical signals from said photo-detector (4) to count a number of particles in said stream by using a predetermined calibration curve; and wherein said cell has a cross sectional area at least as great as a maximum cross sectional area in portions of said stream of fluid upstream and downstream relative to said cell.

10. The apparatus set forth in claim 9 wherein said optical system consists of a lens.

11. The apparatus set forth in claim 9 wherein said coherent light source is a semiconductor laser.

12. The apparatus set forth in claim 9 wherein said photodetector comprises a photo-diode alley arranged perpendicularly to the direction of said stream and also perpendicularly to said optical axis.

13. The apparatus set forth in claim 12 wherein said electric circuit includes differential amplifiers for multiplying signals from elements in said photo-diode alley.

14. The apparatus of claim 9 wherein the light goes directly from the stream of fluid to the photodetector.

15. The apparatus of claim 14 further comprising a focusing lens positioned such that focused light goes directly from the focusing lens to the stream of fluid.

16. The apparatus of claim 9 further comprising a focusing lens positioned such that focused light goes directly from the focusing lens to the stream of fluid.

* * * * *